(12) United States Patent
Summerton et al.

(10) Patent No.: US 6,315,895 B1
(45) Date of Patent: Nov. 13, 2001

(54) DUAL-STAGE HEMODIAFILTRATION CARTRIDGE

(75) Inventors: James Summerton, Hillsdale, NJ (US); Gregory R. Collins, Monroe, NY (US)

(73) Assignee: Nephros, Inc., New York, NY (US)

( * ) Notice: Subject to any disclaimer, the term of this patent is extended or adjusted under 35 U.S.C. 154(b) by 0 days.

(21) Appl. No.: 09/474,855

(22) Filed: Dec. 30, 1999

(51) Int. Cl.$^7$ .......................... B01D 63/00; A61M 37/00
(52) U.S. Cl. .................. 210/96.2; 210/252; 210/321.71; 210/321.8; 210/321.89; 210/323.2; 604/6.09
(58) Field of Search .................. 210/645, 646, 210/650, 252, 321.71, 321.6, 257.2, 420, 323.1, 323.2, 96.2, 321.78, 321.79, 321, 321.87, 321.88, 321.89; 604/6.09

(56) References Cited

U.S. PATENT DOCUMENTS

| | | |
|---|---|---|
| 3,878,095 | 4/1975 | Frasier et al. . |
| 3,946,731 | 3/1976 | Lichtenstein . |
| 3,976,576 | 8/1976 | Jacobsen et al. . |
| 4,038,190 | 7/1977 | Baudet et al. . |
| 4,118,314 | 10/1978 | Yoshida . |
| 4,134,834 | 1/1979 | Brous . |
| 4,219,422 | 8/1980 | Knothe et al. . |
| 4,381,999 | 5/1983 | Boucher et al. . |
| 4,498,990 | 2/1985 | Shaldon et al. . |
| 4,647,378 | 3/1987 | Minami . |
| 5,069,788 | 12/1991 | Radovich et al. . |
| 5,075,003 | * 12/1991 | Aoyagi . |
| 5,178,763 | 1/1993 | Delaunay . |
| 5,194,157 | * 3/1993 | Ghezzi et al. . |
| 5,244,568 | 9/1993 | Lindsay et al. . |
| 5,431,811 | 7/1995 | Tusini et al. . |
| 5,487,827 | 1/1996 | Peterson et al. . |
| 5,660,722 | * 8/1997 | Nederlof . |
| 5,690,831 | 11/1997 | Kenley et al. . |
| 5,725,776 | 3/1998 | Kenley et al. . |
| 5,808,181 | 9/1998 | Wamsiedler et al. . |
| 5,846,419 | 12/1998 | Nederlof . |

FOREIGN PATENT DOCUMENTS

| | | |
|---|---|---|
| 0 018 734 A1 | 11/1980 | (EP) . |
| 0076422 | 4/1983 | (EP) . |
| 0 516 152 A1 | 12/1992 | (EP) . |
| 0 890 368 A1 | 1/1999 | (EP) . |
| 0 960 624 A2 | 12/1999 | (EP) . |
| WO 92/11878 | 7/1992 | (WO) . |
| WO 98/16171 | 4/1998 | (WO) . |
| WO 98/16269 | 4/1998 | (WO) . |
| WO 98/50090 | 11/1998 | (WO) . |
| WO 00/06292 | 2/2000 | (WO) . |
| WO 00/25902 | 5/2000 | (WO) . |
| WO 00/44478 | 8/2000 | (WO) . |

OTHER PUBLICATIONS

"Thoughts and Progress", *Artificial Organs*, 11(2):188–190, New York, 1987.

(List continued on next page.)

*Primary Examiner*—Joseph W. Drodge
*Assistant Examiner*—Terry K Cecil
(74) *Attorney, Agent, or Firm*—Darby & Darby

(57) ABSTRACT

A dual-stage hemodiafiltration cartridge is presented and includes a first hemodiafiltration stage including a first housing with first filtering elements disposed therein. The first housing has a blood inlet and a first dialysate outlet at one end and a first dialysate inlet at an opposite end. The cartridge further includes a second hemodiafiltration stage having a second housing with second filtering elements disposed therein. One end of the second housing has a blood outlet and a second dialysate inlet. An opposite end has a second dialysate outlet. An inter-stage connector is connected to one end of the first housing and to one end of the second housing and is adapted to allow flow of blood from a blood side of said first filtering elements to a blood-side of the second filtering elements and flow of dialysate fluid therethrough from the second stage to the first stage.

19 Claims, 3 Drawing Sheets

OTHER PUBLICATIONS

"Centralized On–Line Hemodiafiltration System Utilizing Purified Dialysate as Substitution Fluid", *Artificial Organs,* 22(4):285–290, 1998.

Albertini, B. von et al.: 2nd Annual Workshop of the International Society of Hemofiltration. Blood Purification 2:44–64 (1984).

Basile, Carlo et al.: Hypertonic hemodiafiltration: A preliminary report on a cross–over study. Kidney International, vol. 33, Suppl. 24 (1988), pp. S–132–S–134.

Basile, Carlo et al.: Plasma Volume Changes Induced by Hypertonic Hemodiafiltration and Standard Hemodialysis. Am. J. Nephrol. 7:264–269 (1987).

Canand, B. et al.: Hemodiafiltration with On–Line Production of Substitution Fluid: Long–Term Safety and Quantitative Assessment of Efficacy. Maeda K. Shinzato T (eds): Effective Hemodiafiltration:New Methods. Contrib Nephrol. Baser, Karger, 1994, vol. 108, pp. 12–22.

Ghezzi, P.M. et al.: Hemodiafiltration Without Replacement Fluid. ASAIO Journal 1992.

Ghezzi, P.M. et al.: Use of the ultrafiltrate obtained in two–chamber (PFD) hemodiafiltration as replacement fluid. The International Journal of Artificial Organs/vol. 14/No.6, 1991/pp.327–334.

Kim, Sung–Teh: Characteristics of Protein removal in Hemodifiltration. Maeda K. Shinzato T (eds.): Effective Hemodiafiltration:New Methods. Contrib Nephrol. Baser, Karger, 1994, vol. 108, pp.23–37.

Maeda, Kenji et al.: Push/Pull Hemodiafiltration: Technical Aspects and Clinical Effectiveness. Nephron 1995:71:1–9.

Man, N.K. et al.: Acetate–Free Biofiltration:State of the Art. Maeda K. Shinzato T (eds): Effective Hemodiafiltration:New Methods. Contrib Nephrol. Baser, Karger, 1994, vol. 108, pp.87–93.

Marangoni, Roberto et al.: Short Time Treatment with High–Efficiency Paired Filtration Dialysis for Chronic Renal Failure. Artificial Organs—6(6):547–552, Blackwell Scientific Publications, Inc., Boston 1992 International Society for Artificial Organs.

Ono, Masataka et al.: Comparison of Types of On–Line Hemodiafiltration from the Standpoint of Low–Molecular-Weight Protein Removal. Maeda K. Shinzato T (eds): Effective Hemodiafiltration:New Methods. Contrib. Nephrol. Baser, Karger, 1994, vol. 108, pp.38–45.

Ronco, C. et al.: Comparison of four different short dialysis techniques. The International Journal of Artificial Organs./vol.11/No.3. 1988/pp.169–174.

Ronco, C. et al.: Paired Filtration Dialysis; Studies: Studies of Efficiency, Flow Dynamics and Hydraulic Properties of the System. Blood Purif 1990; 8:126–140.

Rotellar, Emilio et al.: Large–Surface Hemodialysis. Artificial Organs 10(5):387–396, Raven Press, New York, 1986 International Society for Artificial Organs.

Sanz–Moreno, C. et al.: Hemodiafiltration in Two Chambers Without Replacement Fluid: A Clinical Study. Artificial Organs 19(5):407–410 Blackwell Scientific Publications, Inc., Boston 1995 International Society for Artificial Organs.

Shaldon, S. et al.: Mixed Hemofiltration (MHF): 18 Months With Ultrashort Treatment Time. vol. XXVII Trans Am Soc Artif Intern Organs 1981, pp. 610–612.

Shinzato, Toru et al.: Newly Developed Economical and Efficient Push/Pull Hemodiafiltration. Maeda K. Shinzato T (eds): Effective Hemodiafiltration:New Methods. Contrib Nephrol. Baser, Karger, 1994, vol. 108, pp.79–86.

Sternby, Jan: A Decade of Experience with On–Line Hemofiltration/Hemodiafiltration. Maeda K. Shinzato T (eds): Effective Hemodiafiltration:New Methods. Contrib Nephrol. Baser, Karger, 1994, vol. 108, pp.1–11.

Tsuruta, Kazuma et al.: A Simple Method for Clinical Application Push/Pull Hemodiafiltration. Maeda K. Shinzato T (eds): Effective Hemodiafiltration:New Methods. Contrib Nephrol. Baser, Karger, 1994, vol. 108, pp.71–78.

Usuda, M. et al.: New Simultaneous HF and HD With No Infusion Fluid. vol. XXVIII Trans Am Soc Artif Intern Organs 1982.

Vanholder et al.: In vivo solute elimination of paired filtration dialysis. The International Journal of Artificial Organs/vol. 14/No.1, 1991/pp.23–27.

Zucchelli, P. et al.: Paired Filtration Dialysis: Optimizing Depurative Efficiency with Separate Convection and Diffusion Processes. Nephron 1990; 56:166–173.

* cited by examiner

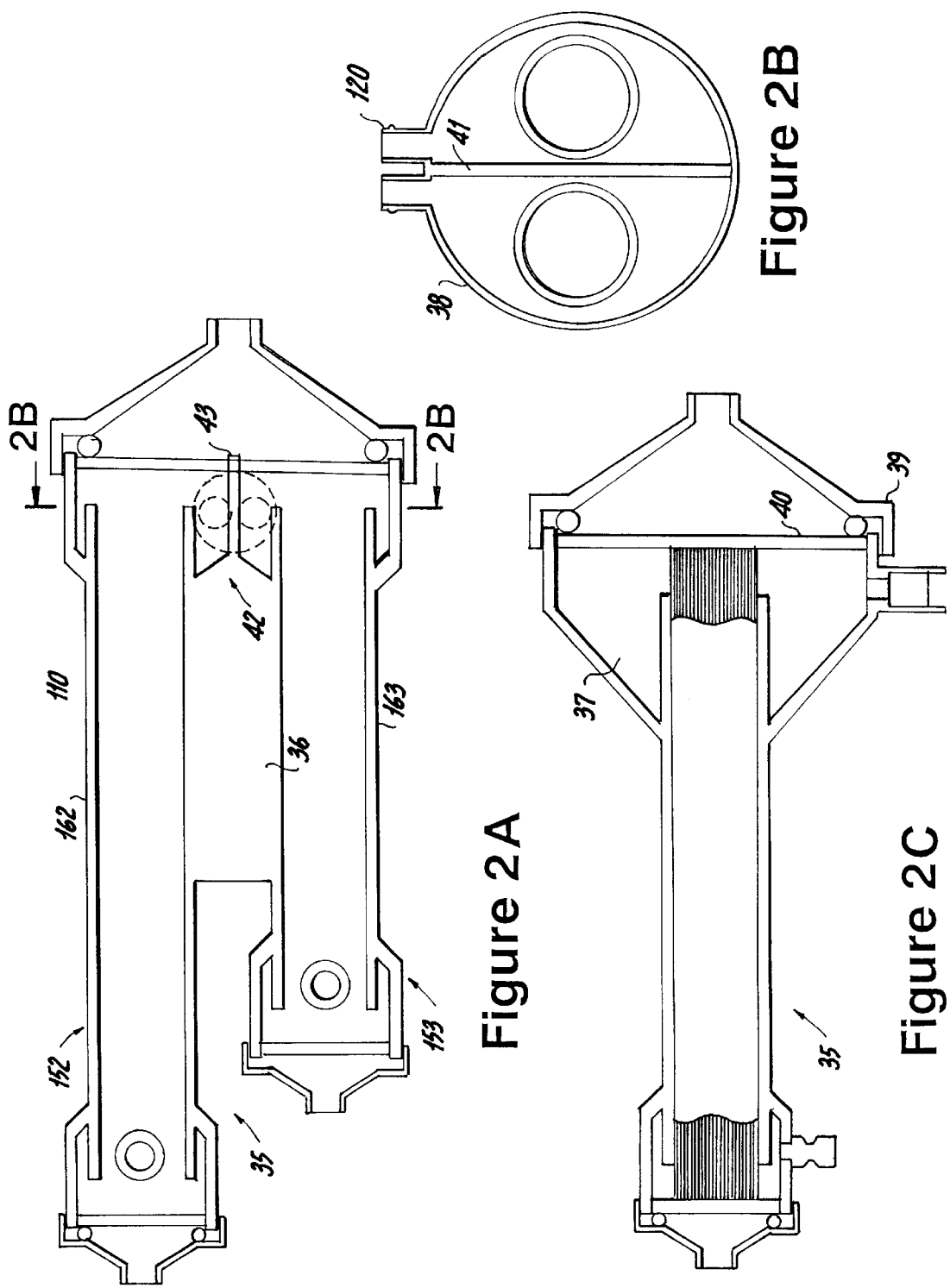

DUAL-STAGE HEMODIAFILTRATION CARTRIDGE

FIELD OF THE INVENTION

The present invention relates to hemodiafiltration devices and methods and, more particularly, to a new hemodiafiltration cartridge and its method of use.

BACKGROUND OF INVENTION

Current treatment for End Stage Renal Disease (ESRD) essentially consists of hemodialysis process, wherein blood to be cleaned flows on one side of a semipermeable membrane and a physiologic solution, a dialysate, flows on the other side of the membrane, whereby toxins in the blood are transferred from one side to the other. The primary driving force in this treatment is diffusion. This process is generally effective in removing small Molecular Weight (MW) toxins such as urea and creatinine. However, this process is much less effective in removing middle range MW substances, e.g., substances having a molecular weight higher than about 1 kDa, because of a low diffusion coefficient of such substances.

To a much lesser extent hemodiafiltration is used as a treatment modality. In hemodiafiltration, diffusion is combined with filtration to remove toxins from the blood. Sterile non-pyrogenic replacement fluid is added to the blood either prior to or after it enters a hemodiafiltration cartridge. The replacement fluid replaces plasma water which is filtered across the semi-permeable membrane during the hemodiafiltration process. The advantage of hemodiafiltration over hemodialysis is the use of filtration in conjunction with diffusion to remove toxins. As a result of this combination, hemodiafiltration is more efficient at removing small molecules, e.g., creatinine and urea, as well as removing much greater quantities of middle range MW substances, by filtration.

State of the art designs for hemodiafiltration filters are substantially equivalent to those of high flux dialyzers. Such filters consist of bundles of hollow fibers in a cylindrical housing. During operation of the hemodiafiltration system, replacement fluid is injected into the blood either upstream (pre-dilution) or downstream (post-dilution) of the filter cartridge.

Diafiltration devices using pre-dilution or post-dilution schemes have inherent efficiency limitations. Pre-dilution schemes allow for relatively unlimited filtration, however, because the blood is diluted prior to reaching the filter, the overall mass transfer of solutes is decreased. Post-dilution schemes have the advantage of keeping blood concentrations high, resulting in more efficient diffusion and convection of solutes, however, the increased concentration of blood cells and the resultant higher blood viscosity during filtration, poses a limit on the amount of water that can be filtered.

SUMMARY OF INVENTION

It is an object of some aspects of the present invention to provide a hemodiafiltration cartridge that enables a higher toxin removal rate and higher toxin removal efficiency than that of prior art hemodiafiltration devices. The present invention reduces and/or eliminates the above mentioned drawbacks of prior art hemodiafiltration devices by providing a scheme in which blood is diluted after it is partially, but not fully, diafiltered. The scheme of the present invention combines the benefits of predilution schemes, e.g., high filtration rate, with the benefits of post dilution schemes, e.g., high diffusive and convective efficiencies. The device of the present invention may be adapted to operate in conjunction with a dual-stage hemodiafiltration machine, or a standard dialysis machine using dual-stage hemodiafiltration, such as the machines described in PCT patent application No. PCT/US99/17468 and in PCT patent application No. PCT/US99/25804, assigned to the assignee of the present application, the disclosures of both of which are incorporated herein by reference in their entirety. Alternatively, by making appropriate alterations in a dual-stage device according to the present invention, e.g., by allowing direct flow of dialysate fluid between the two stages of the dual-stage device, the present invention may be adapted for use in conjunction with a standard dialysis machine using single stage diafiltration.

A hemodiafiltration cartridge in accordance with the present invention has blood and dialysate inlet and outlet ports. The cartridge of the present invention includes two housings, for example, two cylindrical housings, corresponding to two hemodiafiltration stages, wherein the first stage has a blood inlet and a dialysate outlet, and the second stage has a blood outlet and dialysate inlet.

In an embodiment of the present invention, the blood inlet and outlet ports and the dialysate inlet and outlet ports are located on one side, e.g., at the top, of the cartridge. Each of the two hemodiafiltration stages of the present invention may contain longitudinal bundles of high flux, semi-permeable, hollow fibers, which may be sealed off from the dialysate compartments at each end by a potting compound such as polyurethane. The blood inlet may include a header member that may be attached to a casing of the cartridge, at the fiber ends.

In one embodiment, the two stages are produced separately and then assembled together. Alternatively, the two stages may be manufactured as a single unit. The method of production does not affect the resultant dual-stage cartridge.

In an embodiment of the present invention, the cartridge includes two additional ports, preferably at the second end, e.g., the bottom end, of the cartridge. One of these additional ports may be a substitution fluid inlet where sterile replacement fluid is mixed with the blood. This mixing may take place in a common header space, between the first and second stages, where the blood exits the hollow fibers of the first stage and enters the fibers of the second stage.

The other additional port may be an inter-dialysate port, for example, a dual aperture port, which directs dialysate fluid exiting the second stage of the cartridge to cycle through the controlling machine, where the flow rate of the dialysate may be metered, and returns the dialysate to the first stage. While the total level of filtration of the cartridge is generally controlled by the dialysate inlet and outlet rates, the inter-dialysate port enables control of the individual filtration rates of the two cartridge stages. This port may also enable modification of the dialysate flow rate or dialysate composition between the two stages. In an alternative embodiment of the invention, the dialysate fluid exiting the second stage may be directed to flow directly into the first stage, e.g., by providing an aperture-connecting cap to the dual-aperture port.

BRIEF DESCRIPTION OF THE DRAWINGS

FIG. 2A is a schematic, cross-sectional, front view, illustration of a dual stage hemodiafiltration cartridge in accordance with another preferred embodiment of the present invention;

FIG. 2B is a schematic, cross-sectional, top view, illustration of the dual stage hemodiafiltration cartridge of FIG. 2A, taken along section lines 2B—2B;

FIG. 2C is a schematic, cross-sectional, side view, illustration of the dual stage hemodiafiltration cartridge of FIG. 2A;

DETAILED DESCRIPTION OF PREFERRED EMBODIMENTS

Figure 1A:
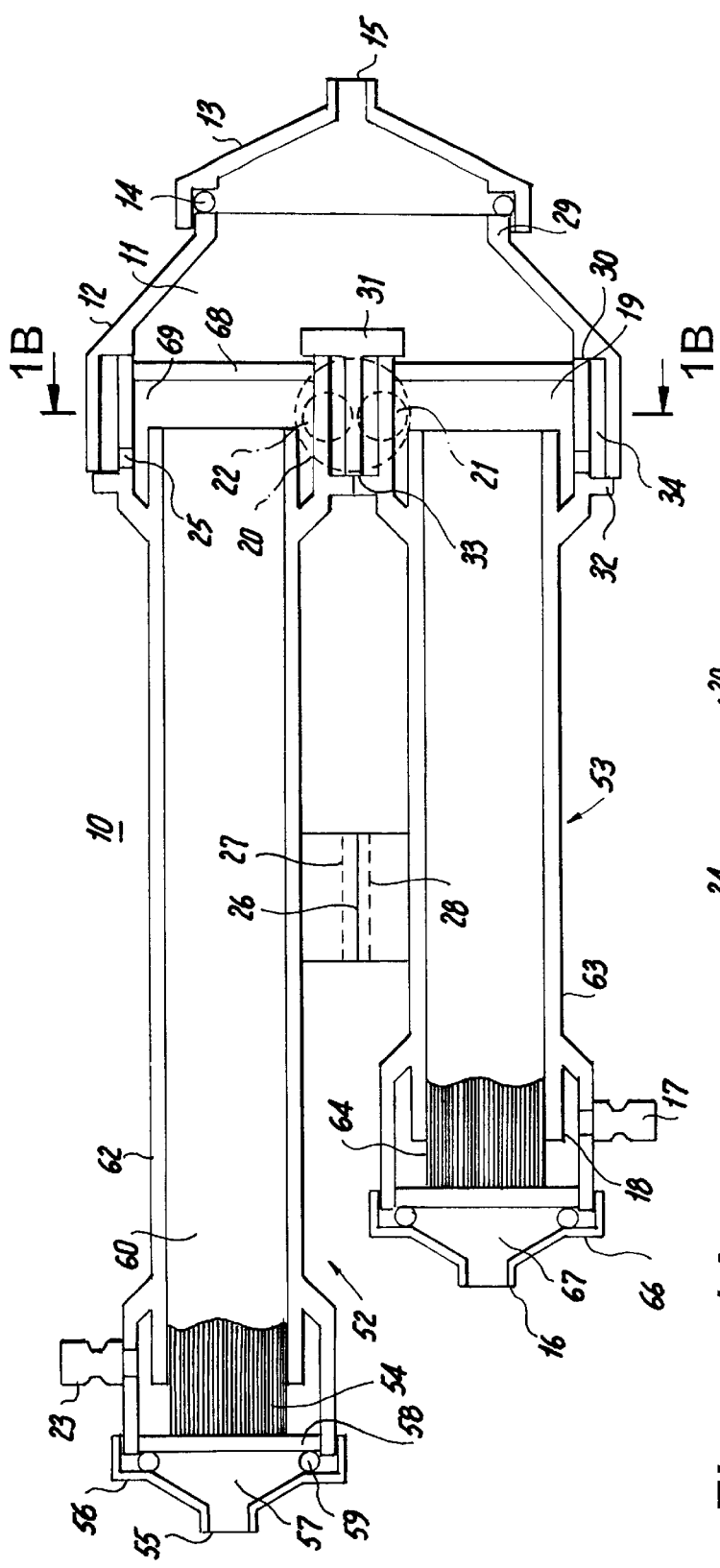
FIG. 1A is a schematic, cross-sectional, front view, illustration of a dual stage hemodliafiltration cartridge in accordance with one preferred embodiment of the present invention.
Figure 1B:
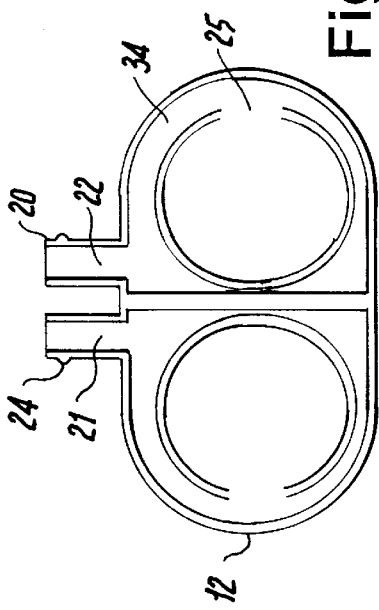
FIG. 1B is a schematic, cross-sectional, top view, illustration of the dual stage hemodiafiltration cartridge of FIG. 1A, taken along section lines 1B—1B.

Reference is made to FIGS. 1A and 1B which schematically illustrate a cross-sectional front view and a cross-sectional top view, respectively, of a dual stage hemodiafiltration cartridge 10 in accordance with one preferred embodiment of the present invention. Cartridge 10 includes a first stage 52 and a second stage 53. Stages 52 and 53 preferably include generally cylindrical housings, 62 and 63, respectively, of a rigid plastic material. Housings 62 and 63 contain longitudinal bundles of semipermeable hollow fibers 54, as are known in the art. The semipermeable fibers serve as a means for transferring the toxins which are being filtered from the blood.

In an embodiment of the present invention, cartridge 10 is adapted to operate in conjunction with a dual stage-hemodiafiltration machine, or a standard dialysis machine using dual-stage hemodiafiltration, such as the machines described in PCT patent application No. PCT/US99/17468 and/or in PCT patent application No. PCT/US99/25804, the disclosures of both of which are incorporated herein by reference in their entirety.

During operation, blood transferred from the patient, via a blood pump of a dual stage hemodiafiltration machine, enters first stage 52 of cartridge 10 through an inlet port 55 which is preferably formed in a header cap 56 mounted on an inlet end of housing 62. Cap 56 defines an inner header space 57 which may be separated from the rest of the cartridge by a potting compound 58, which forms a seal around the outside surfaces of hollow fibers 54. Header cap 56 may be removable and, in such case, header space 57 is preferably sealed from the external environment by a sealing member, such as an O-ring 59.

As blood traverses down the insides of fibers 54, along a main filtration space 60 of first stage 52, the outsides of fibers 54 are immersed in dialysate. This results in first stage hemodiafiltration of toxins, i.e., both filtration and diffusion, which takes place along the entire length of fibers 54 within filtration space 60. In an embodiment of the present invention, a significant portion, e.g., approximately 40%–60%, of the plasma water is filtered as the blood flows through first stage 52. The partly hemodiafiltered blood exiting first stage 52 enters an inter-stage header space 11 associated with another end of housing 62. The blood entering inter-stage header space 11 is in a hemoconcentrated state, i.e., the level of hematocrit in the blood is increased. In accordance with an embodiment of the invention, filtration space 60 of first stage 52 and a filtration space 61 of second stage 53 are separated from header 11, for example, by a potting compound 68, in analogy to the separation described above with reference to header space 57 and potting compound 58.

Inter-stage header space 11, which acts as a transition stage for blood exiting first stage 52 and entering second stage 53, is defined by a stage connector 12 which is preferably made from rigid plastic material and is attached to both the outlet end of first stage 52 and the inlet end of second stage 53, for example, by bonding or welding. Stage connector 12 encloses and defines header space 11 as well as two separate dialysate spaces, 19 and 69. A removable inter-stage header cap 13 having an inlet port 15 is attached to stage connector 12. Header space 11 may be sealed from the external environment by a sealing member, for example, an O-ring 14.

The blood residing in header space 11 prior to entering second stage 53, is diluted with a physiological sterile solution that enters cartridge 10 via header inlet port 15. The sterile solution may be produced continuously, in an "on-line" manner, or provided from reservoirs, e.g., saline bags, as are known in the art. The blood in inter-stage space 11 is hemodiluted, i.e., the blood hematocrit level is decreased. The hemodiluted blood is then carried by fibers 64 disposed in second stage 53, in a manner similar to that described above with reference to first stage 52. At second stage 53 the blood undergoes further hemodiafiltration. The outlet end of second stage 53 is capped with a header cap 66, defining a header space 67 therein, having a blood outlet port 16, in analogy with the above description of header cap 56.

In an embodiment of the present invention, the blood is diafiltered by cartridge 10 at such a rates so that upon exiting second stage 53, via a blood outlet port 16, the blood hematocrit level is substantially the same as that of the blood entering first stage 52. As in standard hemodialysis processes, small changes in the blood hematocrit level may be required in order to control the net ultrafiltration, as may be necessary to maintain patient fluid balance.

As in standard dialysis processes, the dialysate in the present invention is perfused through cartridge 10 in a "counter-current" direction relative to the flow of blood. The dialysate enters second stage 53 via a dialysate inlet 17. A flow disperser 18 ensures that the dialysate will better perfuse the fiber bundle in second stage 53. An inter-dialysate port 20 is preferably associated with dialysate exit region 19 of second stage 53 and with dialysate inlet region 69 of fist stage 52. Inter-dialysate port 20 (shown more clearly in FIG. 1B) is preferably a dual-aperture port including a second stage outlet 21 and a first stage inlet 22.

Figure 3B:
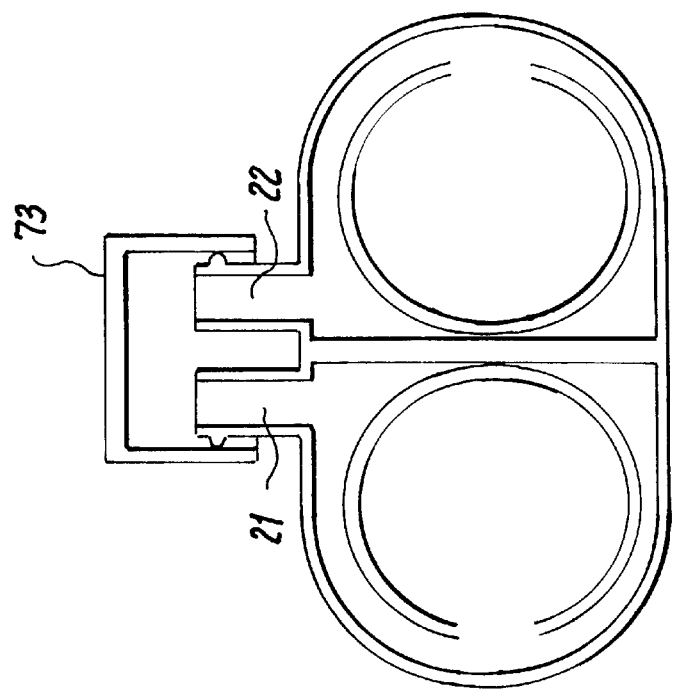
FIG. 3B is a schematic, cross-sectional, top view, illustration of the dual stage hemodiafiltration cartridge of FIG. 1A, taken along section lines 1B—1B, showing connection of a inter-dialysate port of the cartridge to an aperture-connecting cap.
Figure 3A:
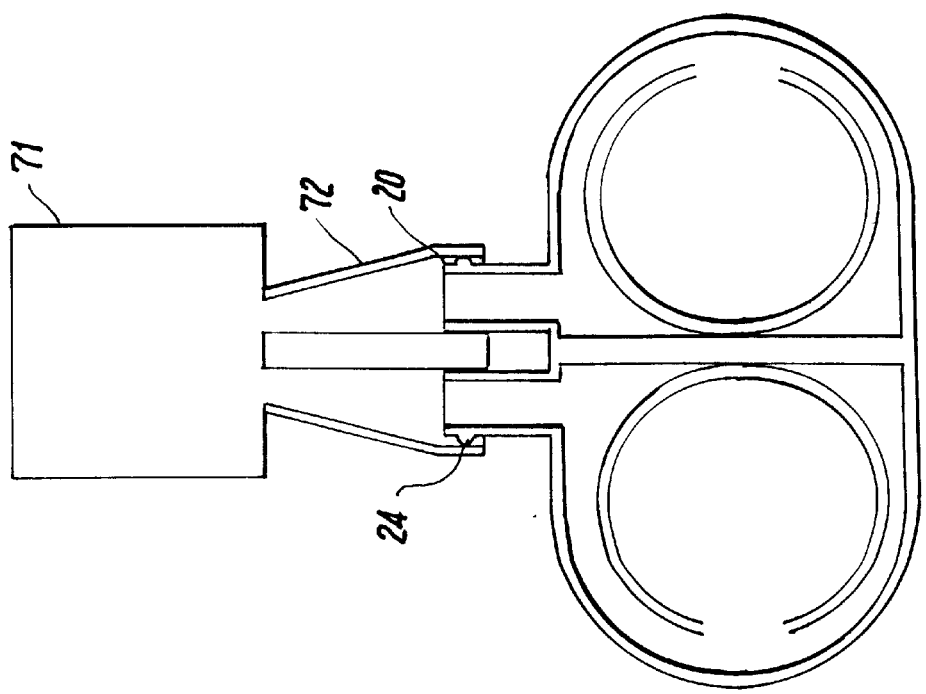
FIG. 3A is a schematic, cross-sectional, top view, illustration of the dual stage hemodiafiltration cartridge of FIG. 1A, taken along section lines 1B—1B, showing connection of an inter-dialysate port of the cartridge to a hemodiafiltration machine.

Reference is now made also to FIG. 3A which schematically illustrates a cross-sectional side view of cartridge 10, showing connection of inter-dialysate port 20 to a hemodiafiltration machine 71, and to FIG. 3B which schematically illustrates a cross-sectional side view of cartridge 10, showing connection of inter-dialysate port 20 to an aperture-connecting cap 73. Machine 71 is preferably a dual-stage hemodiafiltration machine as described. As shown in FIG. 3A, inter-dialysate port 20 may be connected to machine 71 using a dual-aperture connector 24 which is adapted to fit connections 72 on hemodiafiltration machine 71.

In an embodiment of the present invention, hemodiafiltration machine 71 is adapted to monitor the slow and/or dialysate pressures between the first and second stages of cartridge 10. For example, the hemodiafiltration machine may include an inter-dialysate pump (not shown), which may be used to monitor the flow between the first and second stages of cartridge 10 and/or the relative dialysate pressures of the two stages. It should be appreciated, however, that machine 71 may include any other suitable mechanisms, as are know in the art, for controlling dialysate pressure and/or flow. The monitoring of inter-stage flow and/or pressure, enables control of the level of filtration in each of the first and second stages to optimize process efficiency.

Hemodiafiltration machine 71 may also be adapted to monitor and/or control other parameters of the dialysate fluid, between the first and second stages, as described in PCT application No. PCT/US99/17468 and in PCT application No. PCT/US99/25804. For example, the composition and/or salt concentration of the dialysate may be modified between the two stages as described in PCT/US99/25804.

After passing through both hemodiafiltration stages, either directly or via machine 71, as described above, the used dialysate exits cartridge 10 via a dialysate outlet 23 of first stage 52.

Blood inlet and outlet ports 55 and 16, respectively, may be associated with locking connectors, as are known in the art, designed to mate with standard bloodlines. Dialysate inlet port 17 and dialysate outlet port 23 may be associated with standard Hansen connectors, as are know in the art. Substitution fluid inlet port 15 may be associated with a standard luer, e.g., a 6% tapered connector as specified in the ISO 594, adapted to accommodate an IV set, as is known in the art.

To accommodate a dialyzer reuse machines having blood inlet and outlet ports, as are know in the art, substitution fluid inlet port 15 may be capped during reuse. The use of removable header caps 56, 66 and 13, as described above, enables tubesheet cleaning during reuse. Additionally, inter-dialysate port 20 may be fitted with the aperture-connecting cap 73 (FIG. 3B) which allows direct dialysate flow from second stage 53 to first stage 52. Cap 73 seals inter-dialysate port 20 from the external environment while allowing flow of dialysate between dialysate outlet 21 of stage 53 and dialysate inlet 22 of stage 52. Such sealing may be useful during reuse, whereby a dialyzer reuse machine may communicate with cartridge 10 as if it were a standard dialyzer. By allowing direct dialysate flow between the first and second stages, as described above, cartridge 10 may be used in conjunction with a standard dialysis machine, i.e., a dialysis machine designed to operate with a single-stage dialyzer.

A thread or any other suitable locking mechanism, as is known in the art, may be provided on the exterior surface of outlet port 24 to enable tight sealing of port 24 with either the dialysis machine connector 72 or aperture-connecting cap 73.

In the embodiment of FIGS. 1A and 1B, the first and second stages may be manufactured separately and assembled together prior to packaging. Each of housings 62 and 63 is stuffed with a fiber bundle as described above, and may be centrifugally potted as is known in the art. A potting compound, for example, polyurethane resin, may be introduced into first stage 52 via dialysate outlet port 23. At the other end of first stage 52, the potting compound may be introduced via a dedicated potting port 25 which is analogous to the opening of a second dialysate port in conventional dialyzers. The assembly procedure for second stage 53 is analogous to that of first stage 52. Thus, standard potting techniques and equipment may be used in the assembly of the cartridge of the present invention.

To complete the assembly process, the potted ends of the fibers are trimmed to form a smooth tubesheet of open fibers, and the two stages are assembled into a single unit. The final assembly may be preformed as follows. The two stages are locked together, for example, using a "tongue in groove" type bond or weld 26, including a male portion 27 on housing 62 and a female portions 28 on housing 53, or vice versa. This arrangement keeps the housings from being twisted out of alignment. Stage connector 12 may be bonded or welded to the two housings, as mentioned above.

Stage connector 12 may includes inter-dialysate port 20 as well as a mating portion 29 for connecting inter-stage header cap 15. Connector 12 may be circumferentially welded or bonded to housings 62 and 63 at several locations.

A first bond may be formed along the flat ends of the outer rims 30 of housings 62 and 63, where the tubesheet may be encased. This bond seals the blood sides of both stages 52 and 53 from the external environment, but allows free flow through the inter-stage header space 11 between stages 52 and 53. The bond is preferably formed along the entire rim of each housing, including a common central mating portion 31.

A second weld or bond may be formed along external flanges 32 of housings 62 and 63. This bond seals the dialysate potting ports from the external environment and forces all the inter-dialysate flow to go through the inter-dialysate port. Here too there is a common central bond 33 that effectively separates the dialysate compartments of the two stages.

Stage connector 12 is preferably designed such that dialysate may flow out of potting port 25 into an external space 34 around the outside of the stage housings, as well as to the central area where inter-dialysate port 20 is located.

Reference is now made to FIGS. 2A–2C which schematically illustrate a cross-sectional front, a cross-sectional top view and a cross-sectional side-view, respectively, of a dual stage hemodiafiltration cartridge 110 in accordance with another preferred embodiment of the present invention. Most of the elements of cartridge 110, as shown in the embodiment of FIGS. 2A–2C, as well as the features and functions of such elements, are substantially the same as described above with reference to the embodiment of FIGS. 1A and 1B. Cartridge 110 is mounted to a hemodiafiltration machine in the manner described above with reference to the embodiment of FIGS. 1A and 1B.

The difference between the two embodiments is primarily in the structure and assembly of the inter-stage section. In the embodiment of FIGS. 2A–2C, instead of bonding two separately formed cylindrical housings, a dual-housing structure 35 is molded as a single unit, including a first stage housing 162 and a second stage housing 163, for a first hemodiafiltration stage 152 and a second hemodiafiltration stage 153, respectively. This obviates the need for an inter-stage connector and interlocking web, as described above with reference to the embodiment of FIGS. 1A and 1B. These elements of the preceding embodiments are replaced by a common inter-stage molded encasement 37 and a molded web 36, respectively.

Molded structure 35 is preferably formed with an integral, generally circular, end portion 38 which accommodates a removable inter-stage header cap 39. In this arrangement, the entire cross-section of encasement 37 is filled with a potting compound 40, thereby to seal the blood side of the fibers bundled in cartridge 110 from the dialysate side of the fibers. A dual-aperture inter-dialysate port 120, shown particularly in FIG. 2B, is used in this embodiment substantially in the manner described above with reference to port 20 of FIG. 1B. However, in this embodiment, the dialysate of first stage 152 is separated from the dialysate of second stage 153 by a rib member 41 across the entire diameter of inter-stage encasement 37. Rib 41 may be molded to one end 42 of web 36 and sealed to the potting compound at the other end 43.

It will be appreciated by persons skilled in the art that the present invention is not limited to the embodiments described thus far with reference to the accompanying drawing. Rather the present invention is limited only by the following claims.

What is claimed:

1. A dual-stage hemodiafiltration cartridge comprising:
   a first hemodiafiltration stage including a first housing having first and second ends and first filtering elements disposed between the first and second ends, the first end being associated with a blood inlet which allows flow of blood into a blood-side of said first filtering elements and a first dialysate outlet which allows flow of dialysate out of a dialysate-side of said first filtering elements and the second end being associated with a first dialysate inlet which allows flow of dialysate into a dialysate-side of said first filtering elements;
   a second hemodiafiltration stage including a second housing having third and fourth ends and second filtering elements disposed between the third and fourth ends, the fourth end being associated with a blood outlet which allows flow of blood out of a blood-side of said second filtering elements and a second dialysate inlet which allows flow of dialysate into a dialysate-side of said second filtering elements and the third end being associated with a second dialysate outlet which allows flow of dialysate out of the dialysate-side of said second filtering elements; and
   an inter-stage connector connected to the second end of the first housing and to the third end of the second housing and adapted to allow flow of blood from the blood side of the first filtering elements to the blood-side of the second filtering elements and flow of dialysate fluid therethrough from the second stage to the first stage,
   wherein said inter-stage connector has a header space in communication with the blood-side of the first filtering elements and with the blood-side of the second filtering elements, the inter-stage connector having a substitution-fluid inlet which allows flow of substitution fluid into said header space thereby to dilute the blood in said header space.

2. A dual-stage hemodiafiltration cartridge according to claim 1 wherein said inter-stage connector comprises an inter-dialysate port including said first dialysate inlet and said second dialysate outlet.

3. A dual-stage hemodiafiltration cartridge comprising:
   a first hemodiafiltration stage including a first housing having first and second ends and first filtering elements disposed between the first and second ends, the first end being associated with a blood inlet which allows flow of blood into a blood-side of said first filtering elements and a first dialysate outlet which allows flow of dialysate out of a dialysate-side of said first filtering elements and the second end being associated with a first dialysate inlet which allows flow of dialysate into a dialysate-side of said first filtering elements;
   a second hemodiafiltration stage including a second housing having third and fourth ends and second filtering elements disposed between the third and fourth ends, the fourth end being associated with a blood outlet which allows flow of blood out of a blood-side of said second filtering elements and a second dialysate inlet which allows flow of dialysate into a dialysate-side of said second filtering elements and the third end being associated with a second dialysate outlet which allows flow of dialysate out of the dialysate-side of said second filtering elements; and
   an inter-stage connector connected the second end of the first housing and to the third end of the second housing and adapted to allow flow of blood from the blood side of the first filtering elements to the blood-side of the second filtering elements,
   wherein said inter-stage connector has a header space in communication with the blood-side of the first filtering elements and with the blood-side of the second filtering elements, the inter-stage connector having a substitution-fluid inlet which allows flow of substitution fluid into said header space thereby to dilute the blood in said header space, the inter-stage connector comprising an inter-dialysate port including said first dialysate inlet and said second dialysate outlet, the cartridge including an inter-aperture cap mounted on said inter-dialysate port and structured to allow flow of dialysate directly from the second dialysate outlet to the first dialysate inlet.

4. A hemodiafiltration system comprising:
   a dual-stage hemodiafiltration cartridge according to claim 1; and
   a control mechanism adapted to receive dialysate from the second dialysate outlet and to supply dialysate to the first dialysate inlet,
   wherein said control mechanism controls the relative toxin removal rates of said first and second hemodiafiltration stages.

5. A dual-stage hemodiafiltration cartridge according to claim 1, wherein said first and second housings are arranged parallel to one another with said first end spaced proximately from said fourth end such that the blood flows in a first direction in said first stage and in a second direction in said second stage, said first direction being opposite to said second direction.

6. A dual-stage hemodiafiltration cartridge comprising:
   a first hemodiafiltration stage including a first housing having first and second ends;
   at least one first filtering element disposed between said first and second ends of said first housing, said first end having a blood inlet which communicates with a blood-side of said at least one first filtering element and a first dialysate outlet which is in fluid communication with a dialysate-side of said at least one first filtering element, said second end of said first housing having a first dialysate inlet which admits dialysate into said dialysate-side of said at least one first filtering element;
   a second hemodiafiltration stage including a second housing having third and fourth ends;
   at least one second filtering element disposed between said third and fourth ends of said second housing, said fourth end having a blood outlet for passage of blood out of a blood-side of said at least one second filtering element and a second dialysate inlet which is in fluid communication with a dialysate-side of said at least one second filtering element, said third end having a second dialysate outlet for discharge of dialysate from said dialysate-side of said at least one second filtering element; and a connector connected to said second end of said first housing and to said third end of said second housing for the passage of blood from the blood-side of said at least one first filtering element to the blood-side of said at least one second filtering element, said connector having a fluid inlet for receiving substitution fluid which mixes with the blood from said first stage before the blood flows to said blood-side of said at least one second filtering element of said second stage, said connector adapted to conduct the dialysate from said second stage to said first stage.

7. A dual-stage hemodiafiltration cartridge according to claim 6, wherein said first and second housings are part of a single cartridge member with said connector being integrally formed with said first and second housings.

8. A dual-stage hemodiafiltration cartridge according to claim 6, wherein said connector includes a header space in communication with said blood-side of said at least one first filtering element and with said blood-side of said at least one second filtering element, the substitution fluid flowing in said header space to dilute the blood from said first stage.

9. A dual-stage hemodiafiltration cartridge according to claim 8, further including:

an inter-stage header cap releasably mounted to said connector, said cap having an inlet for receiving substitution fluid.

10. A dual-stage hemodiafiltration cartridge according to claim 9, further including:

a sealing member for sealing said header space from an external environment, said sealing member being disposed between said inter-stage header cap and said connector, thereby sealing said header space.

11. A dual-stage hemodiafiltration cartridge according to claim 6, wherein said connector includes an inter-dialysate port defined at least in part by said first dialysate inlet and said second dialysate outlet, said inter-dialysate port permitting the dialysate to flow from said second stage to said first stage.

12. A dual-stage hemodiafiltration cartridge according to claim 11, further including an inter-aperture cap detachably coupled to said inter-dialysate port and configured to permit the dialysate to flow from said second dialysate outlet to said first dialysate inlet.

13. A dual-stage hemodiafiltration cartridge according to claim 8, wherein said connector includes a member for separating said first and second stages, said member partitioning said header space from said first and second stages, said member communicating with said at least one first and second filtering elements such that said blood-sides of said at least one first and second filtering elements are in fluid communication with said header space to permit the blood to flow from said at least one first filtering element through said header space to said at least one second filtering element.

14. A dual-stage hemodiafiltration cartridge comprising:

a first hemodiafiltration stage including a first housing having first and second ends;

at least one first filtering element disposed between said first and second ends of said first housing, said first end having a blood inlet which communicates with a first side of said at least one first filtering element and a first dialysate outlet which is in fluid communication with a second side of said at least one first filtering element, said second end of said housing having a first dialysate inlet which admits dialysate into said second side of said at least one first filtering element;

a second hemodiafiltration stage including a second housing having third and fourth ends;

at least one second filtering element disposed between said third and fourth ends of said second housing, said fourth end having a blood outlet for passage of blood out of a first side of said at least one second filtering element and a second dialysate inlet which is in fluid communication with a second side of said at least one second filtering element, said third end having a second dialysate outlet for discharge of dialysate from said second side of said at least one second filtering element; and a connector connected to said second end of said first housing and to said third end of said second housing for the passage of blood from the first side of said at least one first filtering element to the first side of said at least one second filtering element, said connector being in fluid communication with the second sides of said at least one first and second filtering elements for passage of dialysate fluid from said second stage to said first stage.

15. A dual-stage hemodiafiltration device cartridge according to claim 14, wherein said connector has a header space in communication with said first side of said at least one first filtering element and with said first side of said at least one second filtering element, said connector having a substitution fluid inlet which allows substitution fluid to flow into said header space.

16. A dual-stage hemodiafiltration cartridge according to claim 14, wherein said connector includes; an inter-dialysate port defined at least in part by said first dialysate inlet and said second dialysate outlet, said inter-dialysate port permitting the dialysate to flow from said second stage to said first stage.

17. A dual-stage hemodiafiltration cartridge according to claim 16, further including an inter-aperture cap detachably coupled to said inter-dialysate port and configured to permit the dialysate to flow from said second dialysate outlet to said first dialysate inlet.

18. A dual-stage hemodiafiltration cartridge comprising:

a first hemodiafiltration stage including a first housing having first and second ends;

at least one first filtering element disposed between said first and second ends of said first housing, said first end having a blood inlet which communicates with a first surface of said at least one first filtering element and a first dialysate outlet which is in fluid communication with a second surface of said at least one first filtering element, said second end of said housing having a first dialysate inlet which admits dialysate to said second surface of said at least one first filtering element;

a second hemodiafiltration stage including a second housing having third and fourth ends;

at least one second filtering element disposed between said third and fourth ends of said second housing, said fourth end having a blood outlet for passage of blood from a first surface of said at least one second filtering element and a second dialysate inlet which admits dialysate to a second surface of said at least one second filtering element, said third end having a second dialysate outlet for discharge of dialysate from said second surface of said at least one second filtering element; and a connector connected to the second end of said first housing and to said third end of said second housing, said connector including a first section for the passage of blood from the first surface of said at least one first filtering element to the first surface of said at least one second filtering element and a second section for passage of dialysate fluid from said second stage to said first stage.

19. A dual-stage hemodiafiltration cartridge according to claim 18, wherein said first section includes a header space in communication with said at least one first and second filtering elements, said connector having a substitution-fluid inlet which allows flow of substitution fluid into said header space resulting in the blood in said header space being diluted, said second section includes an inter-dialysate port defined by said first dialysate inlet and said second dialysate outlet with an inter-aperture cap detachably coupled to said inter-dialysate port and configured so that the dialysate flows directly from said second dialysate outlet to said first dialysate inlet.

\* \* \* \* \*